(12) United States Patent
Thompson

(10) Patent No.: US 12,281,326 B1
(45) Date of Patent: Apr. 22, 2025

(54) COMPOSITION FOR REGULATING PRODUCTION OF PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/990,401

(22) Filed: Dec. 20, 2024

(51) Int. Cl.
*C07K 14/005* (2006.01)
*C12N 15/86* (2006.01)

(52) U.S. Cl.
CPC ............ *C12N 15/86* (2013.01); *C07K 14/005* (2013.01); *C12N 2750/14122* (2013.01); *C12N 2750/14143* (2013.01)

(58) Field of Classification Search
CPC .......... C12N 15/86; C12N 2750/14122; C12N 2750/14143; C07K 14/005
See application file for complete search history.

*Primary Examiner* — Evelyn Y Pyla
*Assistant Examiner* — Katherine R Small
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in the bioavailability of the target biomolecule within a subject that is administered the one or more compositions. In some embodiments of the present disclosure, the target biomolecule is a protein such as AAV capsid protein.

9 Claims, No Drawings

Specification includes a Sequence Listing.

COMPOSITION FOR REGULATING PRODUCTION OF PROTEINS

This application contains a Sequence Listing electronically submitted via Patent Center to the United States Patent and Trademark Office as an XML Document file entitled "G10017336P1US-SequenceListing.xml" created on 2024 Dec. 18 and having a size of 18,022 bytes. The information contained in the Sequence Listing is incorporated by reference herein.

TECHNICAL FIELD

The present disclosure generally relates to compositions for regulating the production of proteins. In particular, the present disclosure relates to compositions for regulating the gene expression and consequently, the production, of proteins that act as viral capsids.

BACKGROUND

Viruses produce capsid proteins that form the structure of the virus.

As such, it may be desirable to establish therapies, treatments and/or interventions that may induce capsid proteins to be endogenously produced in a subject.

SUMMARY

Some embodiments of the present disclosure relate to one or more compositions that upregulate the production of one or more sequences of messenger ribonucleic acid (mRNA). The sequences of mRNA may encode for the translation of a target biomolecule, thereby causing an increase in the bioavailability of the target biomolecule within a subject that is administered the one or more compositions. In some embodiments of the present disclosure, the target biomolecule is a protein such as AAV capsid protein.

In some embodiments of the present disclosure the compositions comprise a plasmid of deoxyribonucleic acid (DNA) that includes one or more insert sequences of nucleotides that encode for the production of mRNA and a backbone sequence of nucleic acids that facilitates the introduction of the one or more insert sequences into one or more of a subject's cells where it is thereby expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding for one or more nucleotide sequences encoding for an mRNA sequence that encodes for AAV capsid protein.

Some embodiments of the present disclosure relate to a method of making a composition/target cell complex. The method comprises a step of administering an RP comprising SEQ ID NO. 1 and SEQ ID NO. 2 to a target cell for forming a composition/target cell complex, wherein the composition/target cell complex causes the target cell to increase the production of one or more sequences of mRNA that consequently increases the production of a target biomolecule.

Embodiments of the present disclosure relate to at least one approach for inducing the endogenous production of one or more sequences of mRNA that encodes for a target biomolecule, for example an AAV capsid protein. A first approach utilizes gene vectors containing nucleotide sequences for increasing the endogenous production of one or more sequences of mRNA, which are complete or partial sequences of AAV capsid protein and/or combinations thereof, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present disclosure. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, the composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for the production of at least one sequence of mRNA that increases the production of target biomolecules, such as a protein.

In some embodiments of the present disclosure, the target biomolecule is AAV capsid protein.

Some embodiments of the present disclosure relate to a composition that can be administered to a subject with a condition that results, directly or indirectly, from the dysregulated production of a biomolecule. When a therapeutically effective amount of the composition is administered to the subject, the production and/or functionality of one or more of the subject's biomolecules may change as a result.

In some embodiments of the present disclosure, the production and/or functionality of one or more of the subject's intermediary molecules may change in response to the subject receiving a therapeutic amount of the composition, thereby changing production of one or more DNA sequences, one or more RNA sequences, and/or one or more proteins that regulate the levels and/or functionality of the one or more intermediary molecules. The one or more intermediary molecules may regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as AAV capsid protein.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

Some embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID50/kg (50% tissue culture infective dose per kilogram of the patient's body mass). In some embodiments of the present disclosure, the therapeutically effective amount of the composition that is administered to the patient is about $1\times10^{13}$ TCID50/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that, when operable inside a target cell, will cause the target cell to produce an mRNA sequence that upregulates the production of a biomolecule, with an example being AAV capsid protein. The RP is comprised of AAV2 inverted terminal repeats (ITRs), a composite CASI promoter, and a human growth hormone (HGH) signal peptide followed by a mRNA expression cassette encoding for AAV capsid protein, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):
5'

ACCATGTTCATGTTTTCTTTTTTTTCTACAGGTCCTGGGTGACGAACAGGGTACCAA

GATCTAACTTGTTTATTGCAGCTTATAATGGTTACAAATAAAGCAATAGCATCACAA

ATTTCACAAATAAAGCATTTTTTTCACTGCATTCTAGTTGTGGTTTGTCCAAACTCAT

CAATGTATCTTATCATGTCTGGATCTCGACCTCGACTAGAGCATGGCTACGTAGATA

AGTAGCATGGCGGGTTAATCATTAACTACAAGGAACCCCTAGTGATGGAGTTGGCC

ACTCCCTCTCTGCGCGCTCGCTCGCTCACTGAGGCCGGGCGACCAAAGGTCGCCCGA

CGCCCGGGCTTTGCCCGGGCGGCCTCAGTGAGCGAGCGAGCGCGCAGCTGGCGTAA

TAGCGAAGAGGCCCGCACCGATCGCCCTTCCCAACAGTTGCGCAGCCTGAATGGCG

AATGGCGATTCCGTTGCAATGGCTGGCGGTAATATTGTTCTGGATATTACCAGCAAG

GCCGATAGTTTGAGTTCTTCTACTCAGGCAAGTGATGTTATTACTAATCAAAGAAGT

ATTGCGACAACGGTTAATTTGCGTGATGGACAGACTCTTTTACTCGGTGGCCTCACT

GATTATAAAAACACTTCTCAGGATTCTGGCGTACCGTTCCTGTCTAAAATCCCTTTAA

TCGGCCTCCTGTTTAGCTCCCGCTCTGATTCTAACGAGGAAAGCACGTTATACGTGC

TCGTCAAAGCAACCATAGTACGCGCCCTGTAGCGGCGCATTAAGCGCGGCGGGTGT

GGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAAT

CGGGGGCTCCCTTTAGGGTTCCGATTTAGTGCTTTACGGCACCTCGACCCCAAAAAA

CTTGATTAGGGTGATGGTTCACGTAGTGGGCCATCGCCCTGATAGACGGTTTTCGC

CCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGCCGATTTCGG

CCTATTGGTTAAAAAATGAGCTGATTTAACAAAAATTTAACGCGAATTTTAACAAAA

TATTAACGTTTACAATTTAAATATTTGCTTATACAATCTTCCTGTTTTTGGGGCTTTTC

TGATTATCAACCGGGGTACATATGATTGACATGCTAGTTTTACGATTACCGTTCATC

GATTCTCTTGTTTGCTCCAGACTCTCAGGCAATGACCTGATAGCCTTTGTAGAGACCT

CTCAAAAATAGCTACCCTCTCCGGCATGAATTTATCAGCTAGAACGGTTGAATATCA

TATTGATGGTGATTTGACTGTCTCCGGCCTTTCTCACCCGTTTGAATCTTTACCTACA

CATTACTCAGGCATTGCATTTAAAATATATGAGGGTTCTAAAAATTTTTATCCTTGCG

TTGAAATAAAGGCTTCTCCCGCAAAAGTATTACAGGGTCATAATGTTTTTGGTACAA

CCGATTTAGCTTTATGCTCTGAGGCTTTATTGCTTAATTTTGCTAATTCTTTGCCTTGC

CTGTATGATTTATTGGATGTTGGAATTCCTGATGCGGTATTTTCTCCTTACGCATCTG

-continued

```
TGCGGTATTTCACACCGCATATGGTGCACTCTCAGTACAATCTGCTCTGATGCCGCA

TAGTTAAGCCAGCCCCGACACCCGCCAACACCCGCTGACGCGCCCTGACGGGCTTGT

CTGCTCCCGGCATCCGCTTACAGACAAGCTGTGACCGTCTCCGGGAGCTGCATGTGT

CAGAGGTTTTCACCGTCATCACCGAAACGCGCGAGACGAAAGGGCCTCGTGATACG

CCTATTTTTATAGGTTAATGTCATGATAATAATGGTTTCTTAGACGTCAGGTGGCACT

TTTCGGGGAAATGTGCGCGGAACCCCTATTTGTTTATTTTTCTAAATACATTCAAATA

TGTATCCGCTCATGAGACAATAACCCTGATAAATGCTTCAATAATATTGAAAAGGA

AGAGTATGAGTATTCAACATTTCCGTGTCGCCCTTATTCCCTTTTTTGCGGCATTTTG

CCTTCCTGTTTTTGCTCACCCAGAAACGCTGGTGAAAGTAAAAGATGCTGAAGATCA

GTTGGGTGCACGAGTGGGTTACATCGAACTGGATCTCAACAGCGGTAAGATCCTTGA

GAGTTTTCGCCCCGAAGAACGTTTTCCAATGATGAGCACTTTTAAAGTTCTGCTATGT

GGCGCGGTATTATCCCGTATTGACGCCGGGCAAGAGCAACTCGGTCGCCGCATACA

CTATTCTCAGAATGACTTGGTTGAGTACTCACCAGTCACAGAAAAGCATCTTACGGA

TGGCATGACAGTAAGAGAATTATGCAGTGCTGCCATAACCATGAGTGATAACACTG

CGGCCAACTTACTTCTGACAACGATCGGAGGACCGAAGGAGCTAACCGCTTTTTTGC

ACAACATGGGGGATCATGTAACTCGCCTTGATCGTTGGGAACCGGAGCTGAATGAA

GCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGG

CTGGTTTATTGCTGATAAATCTGGAGCCGGTGAGCGTGGGTCTCGCGGTATCATTGC

AGCACTGGGGCCAGATGGTAAGCCCTCCCGTATCGTAGTTATCTACACGACGGGGA

GTCAGGCAACTATGGATGAACGAAATAGACAGATCGCTGAGATAGGTGCCTCACTG

ATTAAGCATTGGTAACTGTCAGACCAAGTTTACTCATATATACTTTAGATTGATTTAA

AACTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAGAT

CAAAGGATCTTCTTGAGATCCTTTTTTTCTGCGCGTAATCTGCTGCTTGCAAACAAAA

AAACCACCGCTACCAGCGGTGGTTTGTTTGCCGGATCAAGAGCTACCAACTCTTTTT

CCGAAGGTAACTGGCTTCAGCAGAGCGCAGATACCAAATACTGTCCTTCTAGTGTAG

CCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTG

GACTCAAGACGATAGTTACCGGATAAGGCGCAGCGGTCGGGCTGAACGGGGGGTTC

GTGCACACAGCCCAGCTTGGAGCGAACGACCTACACCGAACTGAGATACCTACAGC

GTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACG

CCTGGTATCTTTATAGTCCTGTCGGGTTTCGCCACCTCTGACTTGAGCGTCGATTTTT

GTGATGCTCGTCAGGGGGCGGAGCCTATGGAAAAACGCCAGCAACGCGGCCTTTT

TACGGTTCCTGGCCTTTTGCTGGCCTTTTGCTCACATGTTCTTTCCTGCGTTATCCCCT

GATTCTGTGGATAACCGTATTACCGCCTTTGAGTGAGCTGATACCGCTCGCCGCAGC

CGAACGACCGAGCGCAGCGAGTCAGTGAGCGAGGAAGCGGAAGAGCGCCCAATAC

GCAAACCGCCTCTCCCCGCGCGTTGGCCGATTCATTAATGCAGCTGCGCGCTCGCTC
```

-continued

```
GCTCACTGAGGCCGCCCGGGCAAAGCCCGGGCGTCGGGCGACCTTTGGTCGCCCGG
CCTCAGTGAGCGAGCGAGCGCGCAGAGAGGGAGTGGCCAACTCCATCACTAGGGGT
TCCTTGTAGTTAATGATTAACCCGCCATGCTACTTATCTACGTAGCCATGCTCTAGGA
CATTGATTATTGACTAGTGGAGTTCCGCGTTACATAACTTACGGTAAATGGCCCGCC
TGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAAC
TGCCCACTTGGCAGTACATCAAGTGTATCATATGCCAAGTACGCCCCCTATTGACGT
CAATGACGGTAAATGGCCCGCCTGGCATTATGCCCAGTACATGACCTTATGGGACTT
TCCTACTTGGCAGTACATCTACGTATTAGTCATCGCTATTACCATGGTCGAGGTGAG
CCCCACGTTCTGCTTCACTCTCCCCATCTCCCCCCCCTCCCCACCCCCAATTTTGTATT
TATTTATTTTTTAATTATTTTGTGCAGCGATGGGGGCGGGGGGGGGGGGGGCGCGC
GCCAGGCGGGGCGGGGCGGGGCGAGGGGCGGGGCGGGGCGAGGCGGAGAGGTGC
GGCGGCAGCCAATCAGAGCGGCGCGCTCCGAAAGTTTCCTTTTATGGCGAGGCGGC
GGCGGCGGCGGCCCTATAAAAAGCGAAGCGCGCGGCGGGCGGGAGTCGCTGCGCG
CTGCCTTCGCCCCGTGCCCCGCTCCGCCGCCGCCTCGCGCCGCCCGCCCCGGCTCTG
ACTGACCGCGTTACTAAAACAGGTAAGTCCGGCCTCCGCGCCGGGTTTTGGCGCCTC
CCGCGGGCGCCCCCTCCTCACGGCGAGCGCTGCCACGTCAGACGAAGGGCGCAGC
GAGCGTCCTGATCCTTCCGCCCGGACGCTCAGGACAGCGGCCCGCTGCTCATAAGAC
TCGGCCTTAGAACCCCAGTATCAGCAGAAGGACATTTTAGGACGGGACTTGGGTGA
CTCTAGGGCACTGGTTTTCTTTCCAGAGAGCGGAACAGGCGAGGAAAAGTAGTCCCT
TCTCGGCGATTCTGCGGAGGGATCTCCGTGGGGCGGTGAACGCCGATGATGCCTCTA
CTA
3'

SEQ ID NO. 2 (mRNA expression cassette No. 2 - AAV capsid protein):
5'
GCCACCATGGCGGCGGATGGCTATCTGCCGGATTGGCTGGAAGATAACCTGAGCGA
AGGCATTCGCGAATGGTGGGATCTGAAACCGGGCGCGCCGAAACCGAAAGCGAACC
AGCAGAAACAGGATGATGGCCGCGGCCTGGTGCTGCCGGGCTATAAATATCTGGGC
CCGTTTAACGGCCTGGATAAAGGCGAACCGGTGAACGCGGCGGATGCGGCGGCGCT
GGAACATGATAAAGCGTATGATCAGCTGAAAGCGGGCGATAACCCGTATCTGCGCT
ATAACCATGCGGATGCGGAATTTCAGGAACGCCTGCAGGAAGATACCAGCTTTGGC
GGCAACCTGGGCCGCGCGGTGTTTCAGGCGAAAAAACGCGTGCTGGAACCGCTGGG
CCTGGTGGAAGAAGGCGCGAAAACCGCGCCGGGCAAAAAACGCCCGGTGGAACAG
AGCCCGCAGGAACCGGATAGCAGCAGCGGCATTGGCAAAACCGGCCAGCAGCCGG
CGAAAAAACGCCTGAACTTTGGCCAGACCGGCGATAGCGAAAGCGTGCCGGATCCG
CAGCCGCTGGGCGAACCGCCGGCGACCCCGGCGGCGGTGGGCCCGACCACCATGGC
GAGCGGCGGCGGCGCGCCGATGGCGGATAACAACGAAGGCGCGGATGGCGTGGGC
AACGCGAGCGGCAACTGGCATTGCGATAGCACCTGGCTGGGCGATCGCGTGATTAC
CACCAGCACCCGCACCTGGGCGCTGCCGACCTATAACAACCATCTGTATAAACAGA
TTAGCAGCGCGAGCACCGGCGCGAGCAACGATAACCATTATTTTGGCTATAGCACC
CCGTGGGGCTATTTTGATTTTAACCGCTTTCATTGCCATTTTAGCCCGCGCGATTGGC
```

-continued

```
AGCGCCTGATTAACAACAACTGGGGCTTTCGCCCGAAACGCCTGAACTTTAAACTGT
TTAACATTCAGGTGAAAGAAGTGACCACCAACGATGGCGTGACCACCATTGCGAAC
AACCTGACCAGCACCGTGCAGGTGTTTAGCGATAGCGAATATCAGCTGCCGTATGTG
CTGGGCAGCGCGCATCAGGGCTGCCTGCCGCCGTTTCCGGCGGATGTGTTTATGATT
CCGTATGGCTATCTGACCCTGAACAACGGCAGCCAGGCGGTGGGCCGCAGCAGCTT
TTATTGCCTGGAATATTTTCCGAGCCAGATGCTGCGCACCGGCAACAACTTTACCTTT
AGCTATACCTTTGAAGATGTGCCGTTTCATAGCAGCTATGCGCATAGCCAGAGCCTG
GATCGCCTGATGAACCCGCTGATTGATCAGTATCTGTATTTTCTGAACCGCACCCAG
AACCAGAGCGGCAGCGCGCAGAACAAAGATCTGCTGTTTAGCCGCGGCAGCCCGGC
GGGCATGAGCGTGCAGCCGAAAAACTGGCTGCCGGGCCCGTGCTATCGCCAGCGCG
TGAGCAAAACCAAAACCGATAACAACAACAGCAACTTTACCTGGACCGGCGCGAGC
AAATATAACCTGAACGGCCGCGAAAGCATTATTAACCCGGGCACCGCGATGGCGAG
CCATAAAGATGATAAAGATAAATTTTTTCCGATGAGCGGCGTGATGATTTTTGGCAA
AGAAAGCGCGGGCGCGAGCAACACCGCGCTGGATAACGTGATGATTACCGATGAAG
AAGAAATTAAAGCGACCAACCCGGTGGCGACCGAACGCTTTGGCACCGTGGCGGTG
AACCTGCAGAGCAGCAGCACCGATCCGGCGACCGGCGATGTGCATGTGATGGGCGC
GCTGCCGGGCATGGTGTGGCAGGATCGCGATGTGTATCTGCAGGGCCCGATTTGGGC
GAAAATTCCGCATACCGATGGCCATTTTCATCCGAGCCCGCTGATGGGCGGCTTTGG
CCTGAAACATCCGCCGCCGCAGATTCTGATTAAAAACACCCCGGTGCCGGCGAACC
CGCCGGCGGAATTTAGCGCGACCAAATTTGCGAGCTTTATTACCCAGTATAGCACCG
GCCAGGTGAGCGTGGAAATTGAATGGGAACTGCAGAAAGAAAACAGCAAACGCTG
GAACCCGGAAGTGCAGTATACCAGCAACTATGCGAAAAGCGCGAACGTGGATTTTA
CCGTGGATAACAACGGCCTGTATACCGAACCGCGCCCGATTGGCACCCGCTTTCTGA
CCCGCCCGCTGTTCTAGA
3'

SEQ ID NO. 3 = SEQ ID NO. 1 + SEQ ID NO. 2
5'
ACCATGTTCATGTTTTCTTTTTTTTTCTACAGGTCCTGGGTGACGAACAGGGTACCAA
GATCTAACTTGTTTATTGCAGCTTATAATGGTTACAAATAAAGCAATAGCATCACAA
ATTTCACAAATAAAGCATTTTTTTCACTGCATTCTAGTTGTGGTTTGTCCAAACTCAT
CAATGTATCTTATCATGTCTGGATCTCGACCTCGACTAGAGCATGGCTACGTAGATA
AGTAGCATGGCGGGTTAATCATTAACTACAAGGAACCCCTAGTGATGGAGTTGGCC
ACTCCCTCTCTGCGCGCTCGCTCGCTCACTGAGGCCGGGCGACCAAAGGTCGCCCGA
CGCCCGGGCTTTGCCCGGGCGGCCTCAGTGAGCGAGCGAGCGCGCAGCTGGCGTAA
TAGCGAAGAGGCCCGCACCGATCGCCCTTCCCAACAGTTGCGCAGCCTGAATGGCG
AATGGCGATTCCGTTGCAATGGCTGGCGGTAATATTGTTCTGGATATTACCAGCAAG
GCCGATAGTTTGAGTTCTTCTACTCAGGCAAGTGATGTTATTACTAATCAAAGAAGT
ATTGCGACAACGGTTAATTTGCGTGATGGACAGACTCTTTTACTCGGTGGCCTCACT
GATTATAAAAACACTTCTCAGGATTCTGGCGTACCGTTCCTGTCTAAAATCCCTTTAA
TCGGCCTCCTGTTTAGCTCCCGCTCTGATTCTAACGAGGAAAGCACGTTATACGTGC
TCGTCAAAGCAACCATAGTACGCGCCCTGTAGCGGCGCATTAAGCGCGGCGGGTGT
```

-continued

```
GGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAAT
CGGGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGGAACA
ACACTCAACCCTATCTCGGTCTATTCTTTTGATTTATAAGGGATTTTGCCGATTTCGG
CCTATTGGTTAAAAAATGAGCTGATTTAACAAAAATTTAACGCGAATTTTAACAAAA
TATTAACGTTTACAATTTAAATATTTGCTTATACAATCTTCCTGTTTTTGGGGCTTTTC
TGATTATCAACCGGGGTACATATGATTGACATGCTAGTTTTACGATTACCGTTCATC
GATTCTCTTGTTTGCTCCAGACTCTCAGGCAATGACCTGATAGCCTTTGTAGAGACCT
CTCAAAAATAGCTACCCTCTCCGGCATGAATTTATCAGCTAGAACGGTTGAATATCA
TATTGATGGTGATTTGACTGTCTCCGGCCTTTCTCACCCGTTTGAATCTTTACCTACA
CATTACTCAGGCATTGCATTTAAAATATATGAGGGTTCTAAAAATTTTTATCCTTGCG
TTGAAATAAAGGCTTCTCCCGCAAAAGTATTACAGGGTCATAATGTTTTTGGTACAA
CCGATTTAGCTTTATGCTCTGAGGCTTTATTGCTTAATTTTGCTAATTCTTTGCCTTGC
CTGTATGATTTATTGGATGTTGGAATTCCTGATGCGGTATTTTCTCCTTACGCATCTG
TGCGGTATTTCACACCGCATATGGTGCACTCTCAGTACAATCTGCTCTGATGCCGCA
TAGTTAAGCCAGCCCCGACACCCGCCAACACCCGCTGACGCGCCCTGACGGGCTTGT
CTGCTCCCGGCATCCGCTTACAGACAAGCTGTGACCGTCTCCGGGAGCTGCATGTGT
CAGAGGTTTTCACCGTCATCACCGAAACGCGCGAGACGAAAGGGCCTCGTGATACG
CCTATTTTTATAGGTTAATGTCATGATAATAATGGTTTCTTAGACGTCAGGTGGCACT
TTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGA
AGAGTATGAGTATTCAACATTTCCGTGTCGCCCTTATTCCCTTTTTTGCGGCATTTTG
CCTTCCTGTTTTTGCTCACCCAGAAACGCTGGTGAAAGTAAAAGATGCTGAAGATCA
GTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGT
GGCGCGGTATTATCCCGTATTGACGCCGGGCAAGAGCAACTCGGTCGCCGCATACA
CTATTCTCAGAATGACTTGGTTGAGTACTCACCAGTCACAGAAAAGCATCTTACGGA
TGGCATGACAGTAAGAGAATTATGCAGTGCTGCCATAACCATGAGTGATAACACTG
CGGCCAACTTACTTCTGACAACGATCGGAGGACCGAAGGAGCTAACCGCTTTTTTGC
ACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTT
GCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGG
CTGGTTTATTGCTGATAAATCTGGAGCCGGTGAGCGTGGGTCTCGCGGTATCATTGC
AGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTG
ATTAAGCATTGGTAACTGTCAGACCAAGTTTACTCATATATACTTTAGATTGATTTAA
AACTTCATTTTTAATTTAAAAGGATCTAGGTGAAGATCCTTTTTGATAATCTCATGAC
CAAAATCCCTTAACGTGAGTTTTCGTTCCACTGAGCGTCAGACCCCGTAGAAAAGAT
```

-continued

```
CAAAGGATCTTCTTGAGATCCTTTTTTTCTGCGCGTAATCTGCTGCTTGCAAACAAAA

AAACCACCGCTACCAGCGGTGGTTTGTTTGCCGGATCAAGAGCTACCAACTCTTTTT

CCGAAGGTAACTGGCTTCAGCAGAGCGCAGATACCAAATACTGTCCTTCTAGTGTAG

CCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTG

GACTCAAGACGATAGTTACCGGATAAGGCGCAGCGGTCGGGCTGAACGGGGGGTTC

GTGCACACAGCCCAGCTTGGAGCGAACGACCTACACCGAACTGAGATACCTACAGC

GTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACG

CCTGGTATCTTTATAGTCCTGTCGGGTTTCGCCACCTCTGACTTGAGCGTCGATTTTT

GTGATGCTCGTCAGGGGGCGGAGCCTATGGAAAAACGCCAGCAACGCGGCCTTTT

TACGGTTCCTGGCCTTTTGCTGGCCTTTTGCTCACATGTTCTTTCCTGCGTTATCCCCT

GATTCTGTGGATAACCGTATTACCGCCTTTGAGTGAGCTGATACCGCTCGCCGCAGC

CGAACGACCGAGCGCAGCGAGTCAGTGAGCGAGGAAGCGGAAGAGCGCCCAATAC

GCAAACCGCCTCTCCCCGCGCGTTGGCCGATTCATTAATGCAGCTGCGCGCTCGCTC

GCTCACTGAGGCCGCCCGGGCAAAGCCCGGGCGTCGGGCGACCTTTGGTCGCCCGG

CCTCAGTGAGCGAGCGAGCGCGCAGAGAGGGAGTGGCCAACTCCATCACTAGGGGT

TCCTTGTAGTTAATGATTAACCCGCCATGCTACTTATCTACGTAGCCATGCTCTAGGA

CATTGATTATTGACTAGTGGAGTTCCGCGTTACATAACTTACGGTAAATGGCCCGCC

TGGCTGACCGCCCAACGACCCCCGCCCATTGACGTCAATAATGACGTATGTTCCCAT

AGTAACGCCAATAGGGACTTTCCATTGACGTCAATGGGTGGAGTATTTACGGTAAAC

TGCCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGACTT

TCCTACTTGGCAGTACATCTACGTATTAGTCATCGCTATTACCATGGTCGAGGTGAG

CCCCACGTTCTGCTTCACTCTCCCCATCTCCCCCCCCTCCCCACCCCCAATTTTGTATT

TATTTATTTTTTAATTATTTTGTGCAGCGATGGGGGCGGGGGGGGGGGGGCGCGC

GCCAGGCGGGGCGGGGCGGGGCGAGGGGCGGGGCGGGGCGAGGCGGAGAGGTGC

GGCGGCAGCCAATCAGAGCGGCGCGCTCCGAAAGTTTCCTTTTATGGCGAGGCGGC

GGCGGCGGCGGCCCTATAAAAAGCGAAGCGCGCGGCGGGCGGGAGTCGCTGCGCG

CTGCCTTCGCCCCGTGCCCCGCTCCGCCGCCGCCTCGCGCCGCCCGCCCCGGCTCTG

ACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGC

GAGCGTCCTGATCCTTCCGCCCGGACGCTCAGGACAGCGGCCCGCTGCTCATAAGAC

TCGGCCTTAGAACCCCAGTATCAGCAGAAGGACATTTTAGGACGGGACTTGGGTGA

CTCTAGGGCACTGGTTTTCTTTCCAGAGAGCGGAACAGGCGAGGAAAAGTAGTCCCT

TCTCGGCGATTCTGCGGAGGGATCTCCGTGGGCGGTGAACGCCGATGATGCCTCTA

CTAGCCACCATGGCGGCGGATGGCTATCTGCCGGATTGGCTGGAAGATAACCTGAG

CGAAGGCATTCGCGAATGGTGGGATCTGAAACCGGGCGCGCCGAAACCGAAAGCG

AACCAGCAGAAACAGGATGATGGCCGCGGCCTGGTGCTGCCGGGCTATAAATATCT

GGGCCCGTTTAACGGCCTGGATAAAGGCGAACCGGTGAACGCGGCGGATGCGGCGG
```

-continued

```
CGCTGGAACATGATAAAGCGTATGATCAGCTGAAAGCGGGCGATAACCCGTATCTG

CGCTATAACCATGCGGATGCGGAATTTCAGGAACGCCTGCAGGAAGATACCAGCTT

TGGCGGCAACCTGGGCCGCGCGGTGTTTCAGGCGAAAAAACGCGTGCTGGAACCGC

TGGGCCTGGTGGAAGAAGGCGCGAAAACCGCGCCGGGCAAAAAACGCCCGGTGGA

ACAGAGCCCGCAGGAACCGGATAGCAGCAGCGGCATTGGCAAAACCGGCCAGCAG

CCGGCGAAAAAACGCCTGAACTTTGGCCAGACCGGCGATAGCGAAAGCGTGCCGGA

TCCGCAGCCGCTGGGCGAACCGCCGGCGACCCCGGCGGCGGTGGGCCCGACCACCA

TGGCGAGCGGCGGCGGCGCGCCGATGGCGGATAACAACGAAGGCGCGGATGGCGT

GGGCAACGCGAGCGGCAACTGGCATTGCGATAGCACCTGGCTGGGCGATCGCGTGA

TTACCACCAGCACCCGCACCTGGGCGCTGCCGACCTATAACAACCATCTGTATAAAC

AGATTAGCAGCGCGAGCACCGGCGCGAGCAACGATAACCATTATTTTGGCTATAGC

ACCCCGTGGGCTATTTTGATTTTAACCGCTTTCATTGCCATTTTAGCCCGCGCGATT

GGCAGCGCCTGATTAACAACAACTGGGGCTTTCGCCCGAAACGCCTGAACTTTAAA

CTGTTTAACATTCAGGTGAAAGAAGTGACCACCAACGATGGCGTGACCACCATTGC

GAACAACCTGACCAGCACCGTGCAGGTGTTTAGCGATAGCGAATATCAGCTGCCGT

ATGTGCTGGGCAGCGCGCATCAGGGCTGCCTGCCGCCGTTTCCGGCGGATGTGTTTA

TGATTCCGTATGGCTATCTGACCCTGAACAACGGCAGCCAGGCGGTGGGCCGCAGC

AGCTTTTATTGCCTGGAATATTTTCCGAGCCAGATGCTGCGCACCGGCAACAACTTT

ACCTTTAGCTATACCTTTGAAGATGTGCCGTTTCATAGCAGCTATGCGCATAGCCAG

AGCCTGGATCGCCTGATGAACCCGCTGATTGATCAGTATCTGTATTTTCTGAACCGC

ACCCAGAACCAGAGCGGCAGCGCGCAGAACAAAGATCTGCTGTTTAGCCGCGGCAG

CCCGGCGGGCATGAGCGTGCAGCCGAAAAACTGGCTGCCGGGCCCGTGCTATCGCC

AGCGCGTGAGCAAAACCAAAACCGATAACAACAACAGCAACTTTACCTGGACCGGC

GCGAGCAAATATAACCTGAACGGCCGCGAAAGCATTATTAACCCGGGCACCGCGAT

GGCGAGCCATAAAGATGATAAAGATAAATTTTTTCCGATGAGCGGCGTGATGATTTT

TGGCAAAGAAAGCGCGGGCGCGAGCAACACCGCGCTGGATAACGTGATGATTACCG

ATGAAGAAGAAATTAAAGCGACCAACCCGGTGGCGACCGAACGCTTTGGCACCGTG

GCGGTGAACCTGCAGAGCAGCAGCACCGATCCGGCGACCGGCGATGTGCATGTGAT

GGGCGCGCTGCCGGGCATGGTGTGGCAGGATCGCGATGTGTATCTGCAGGGCCCGA

TTTGGGCGAAAATTCCGCATACCGATGGCCATTTTCATCCGAGCCCGCTGATGGGCG

GCTTTGGCCTGAAACATCCGCCGCCGCAGATTCTGATTAAAAACACCCCGGTGCCGG

CGAACCCGCCGGCGGAATTTAGCGCGACCAAATTTGCGAGCTTTATTACCCAGTATA

GCACCGGCCAGGTGAGCGTGGAAATTGAATGGGAACTGCAGAAAGAAAACAGCAA

ACGCTGGAACCCGGAAGTGCAGTATACCAGCAACTATGCGAAAAGCGCGAACGTGG

ATTTTACCGTGGATAACAACGGCCTGTATACCGAACCGCGCCCGATTGGCACCCGCT

TTCTGACCCGCCCGCTGTTCTAGA
```

3'

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the mRNA expression cassette sequences is not necessary in order to have the desired result of increasing the bioavailability of the target biomolecule as a result of the target cell's production of the mRNA sequence that code for the expression of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands of interest were also excised and purified using a gel extraction kit. These PCR products contained the mRNA expression cassettes, in addition to 15 base pair 5' and 3' overhangs that aligned with the ends of the linearized pAVA-00200 backbone. Using in-fusion cloning, the amplified mRNA expression cassettes were integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with a sequence of nucleotides encoding for a sequence of messenger ribonucleic acid (mRNA) that encodes for a protein, wherein the sequence of mRNA is at least 95% identical to SEQ ID NO. 2.

2. The composition of claim 1, wherein the sequence of nucleotides is configured to be delivered to a target cell.

3. The composition of claim 1, wherein the sequence of nucleotides is encased in a protein coat, a lipid vesicle, or any combination thereof.

4. The composition of claim 1, wherein the sequence of nucleotides is encased in a viral vector.

5. The composition of claim 4, wherein the viral vector is one of a double-stranded DNA virus, a single-stranded DNA virus, a single-stranded RNA virus, or a double-stranded RNA virus.

6. The composition of claim 4, wherein the viral vector is an adeno-associated virus (AAV).

7. The composition of claim 1, wherein the protein is an AAV capsid protein.

8. A composition that comprises a recombinant plasmid (RP) with a sequence of nucleotides for encoding a sequence of messenger ribonucleic acid (mRNA) that encodes for a protein, wherein the sequence is at least 95% identical to SEQ ID NO. 3.

9. The composition of claim 7, wherein the protein is an AAV capsid protein.

* * * * *

SEQUENCE LISTING

```
Sequence total quantity: 3
SEQ ID NO: 1            moltype = DNA   length = 5187
FEATURE                 Location/Qualifiers
source                  1..5187
                        mol_type = other DNA
                        organism = synthetic construct
SEQUENCE: 1
accatgttca tgttttcttt ttttttctac aggtcctggg tgacgaacag ggtaccaaga    60
tctaacttgt ttattgcagc ttataatggt tacaaataaa gcaatagcat cacaaatttc   120
acaaataaag catttttttc actgcattct agttgtggtt tgtccaaact catcaatgta   180
tcttatcatg tctggatctc gacctcgact agagcatggc tacgtagata agtagcatgg   240
cgggttaatc attaactaca aggaacccct agtgatggag ttggccactc cctctctgcg   300
cgctcgctcg ctcactgagg ccgggcgacc aaaggtcgcc cgacgcccgg gctttgccgg   360
ggcggcctca gtgagcgagc gagcgcgcag ctggcgtaat agcgaagagg cccgcaccga   420
tcgcccttcc caacagttgc gcagcctgaa tggcgaatgg cgattccgtt gcaatggctg   480
gcggtaatat tgttctggat attaccagca aggccgatag tttgagttct tctactcagg   540
caagtgatgt tattactaat caaagaagta ttgcgacaac ggttaatttg cgtgatggac   600
agactctttt actcggtggc ctcactgatt ataaaaacac ttctcaggat tctggcgtac   660
cgttcctgtc taaaatccct taatcggcc tcctgtttag ctcccgctct gattctaacg   720
aggaaagcac gttatacgtg ctcgtcaaag caaccatagt acgcgccctg tagcggcgca   780
ttaagcgcgg cgggtgtggt ggttacgcgc agcgtgaccg ctacacttgc cagcgcccta   840
gcgcccgctc ctttcgcttt cttcccttcc tttctcgcca cgttcgccgg ctttccccgt   900
caagctctaa atcgggggct ccctttaggg ttccgattta gtgctttacg gcacctcgac   960
cccaaaaaac ttgattaggg tgatggttca cgtagtgggc catcgccctg atagacggtt  1020
tttcgccctt tgacgttgga gtccacgttc tttaatagtg gactcttgtt ccaaactgga  1080
acaacactca accctatctc ggtctattct tttgatttat aagggatttt gccgatttcg  1140
gcctattggt taaaaaatga gctgatttaa caaaaattta acgcgaattt taacaaaata  1200
ttaacgttta caatttaaat atttgcttat acaatcttcc tgttttgg gcttttctga  1260
ttatcaaccg gggtacatat gattgacatg ctagttttac gattaccgtt catcgattct  1320
cttgtttgct ccagactctc aggcaatgac ctgatagcct ttgtagagac ctctcaaaaa  1380
tagctaccct ctccggcatg aatttatcag ctagaacggt tgaatatcat attgatggtg  1440
atttgactgt ctccggcctt tctcacccgt ttgaatcttt acctacacat tactcaggca  1500
ttgcatttaa aatatatgag ggttctaaaa attttttatcc ttgcgttgaa ataaaggctt  1560
ctcccgcaaa agtattacag ggtcataatg ttttttggtac aaccgattta gctttatgct  1620
ctgaggcttt attgcttaat tttgctaatt ctttgccttg cctgtatgat ttattggatg  1680
ttggaattcc tgatgcggta ttttctcctt acgcatctgt gcggtatttc acaccgcata  1740
tggtgcactc tcagtacaat ctgctctgat gccgcatagt taagccagcc ccgacacccg  1800
ccaacaccog ctgacgcgcc ctgacgggct tgtctgctcc cggcatccgc ttacagacaa  1860
gctgtgaccg tctccgggag ctgcatgtgt cagaggtttt caccgtcatc accgaaacgc  1920
gcgagacgaa agggcctcgt gatacgccta ttttatagg ttaatgtcat gataataatg  1980
gtttcttaga cgtcaggtgg cacttttcgg ggaaatgtgc gcggaacccc tatttgttta  2040
tttttctaaa tacattcaaa tatgtatccg ctcatgagac aataaccctg ataaatgctt  2100
caataatatt gaaaaaggaa gagtatgagt attcaacatt tccgtgtcgc ccttattccc  2160
ttttttgcgg catttttgcct tcctgttttt gctcacccag aaacgctggt gaaagtaaaa  2220
gatgctgaag atcagttggg tgcacgagtg ggttacatcg aactggatct caacagcggt  2280
aagatccttg agagttttcg ccccgaagaa cgttttccaa tgatgagcac ttttaaagtt  2340
ctgctatgtg gcgcggtatt atcccgtatt gacgccggc aagagcaact cggtcgccgc  2400
```

```
atacactatt ctcagaatga cttggttgag tactcaccag tcacagaaaa gcatcttacg 2460
gatggcatga cagtaagaga attatgcagt gctgccataa ccatgagtga taacactgcg 2520
gccaacttac ttctgacaac gatcggagga ccgaaggagc taaccgcttt tttgcacaac 2580
atgggggatc atgtaactcg ccttgatcgt tgggaaccgg agctgaatga agccatacca 2640
aacgacgagc gtgacaccac gatgcctgta gcaatgcaac aacgttgcg caaactatta 2700
actggcgaac tacttactct agcttcccgg caacaattaa tagactggat ggaggcggat 2760
aaagttgcag gaccacttct gcgctcggcc cttccggctg gctggtttat tgctgataaa 2820
tctggagccg gtgagcgtgg gtctcgcggt atcattgcag cactgggcc agatggtaag 2880
ccctcccgta tcgtagttat ctacacgacg gggagtcagg caactatgga tgaacgaaat 2940
agacagatcg ctgagatagg tgcctcactg attaagcatt ggtaactgtc agaccaagtt 3000
tactcatata tactttagat tgatttaaaa cttcatttt aatttaaaag gatctaggtg 3060
aagatccttt ttgataatct catgaccaaa atcccttaac gtgagttttc gttccactga 3120
gcgtcagacc ccgtagaaaa gatcaaagga tcttcttgag atcctttttt tctgcgcgta 3180
atctgctgct tgcaaacaaa aaaaccaccg ctaccagcgg tggtttgttt gccggatcaa 3240
gagctaccaa ctcttttcc gaaggtaact ggcttcagca gagcgcagat accaaatact 3300
gtcctttctag tgtagccgta gttaggccac cacttcaaga actctgtagc accgcctaca 3360
tacctcgctc tgctaatcct gttaccagtg gctgctgcca gtggcgataa gtcgtgtctt 3420
accgggttgg actcaagacg atagttaccg gataaggcgc agcggtcggg ctgaacgggg 3480
ggttcgtgca cacagcccag cttggagcga acgacctaca ccgaactgag atacctacag 3540
cgtgagctat gagaaagcgc cacgcttccc gaagggagaa aggcggacag gtatccggta 3600
agcggcaggg tcggaacagg agagcgcacg agggagcttc caggggggaaa cgcctggtat 3660
ctttatagtc ctgtcgggtt tcgccacctc tgacttgagc gtcgattttt gtgatgctcg 3720
tcagggggc ggagcctatg gaaaaacgcc agcaacgcgg cctttttacg gttcctggcc 3780
ttttgctggc cttttgctca catgttcttt cctgcgttat cccctgattc tgtggataac 3840
cgtattaccg cctttgagtg agctgatacc gctcgccgca gccgaacgac cgagcgcagc 3900
gagtcagtga gcgaggaagc ggaagagcgc ccaatacgca aaccgcctct ccccgcgcgt 3960
tggccgattc attaatgcag ctgcgcgctc gctcgctcac tgaggccgcc cgggcaaagc 4020
ccgggcgtcg ggcgaccttt ggtcgcccgg cctcagtgag cgagcgagcg cgcagagagg 4080
gagtggccaa ctccatcact aggggttcct tgtagttaat gattaacccg ccatgctact 4140
tatctacgta gccatgctct aggacattga ttattgacta gtggagttcc gcgttacata 4200
acttacggta aatggcccgc ctggctgacc gcccaacgac ccccgcccat tgacgtcaat 4260
aatgacgtat gttcccatag taacgccaat agggactttc cattgacgtc aatgggtgga 4320
gtatttacgg taaactgccc acttggcagt acatcaagtg tatcatatgc caagtacgcc 4380
ccctattgac gtcaatgacg gtaaatggcc cgcctggcat tatgcccagt acatgacctt 4440
atgggacttt cctacttggc agtacatcta cgtattagtc atcgctatta ccatggtcga 4500
ggtgagcccc acgttctgct tcactctccc catctcccc cctccccac cccaattttt 4560
gtatttattt atttttaat tattttgtgc agcgatgggg gcggggggg gggggggcgc 4620
gcgccaggcg gggcggggcg gggcgagggg cgggcgggg cgaggcggag aggtgcggcg 4680
gcagccaatc agagcgcgc gctccgaaag tttccttta tggcgaggcgg gcggcggcgg 4740
cggccctata aaaagcgaag cgcgcggcgg gcgggagtcg ctgcgcgctg ccttcgcccc 4800
gtgccccgct ccgccgccgc ctcgcgccgc ccgcccggc tctgactgac cgcgttacta 4860
aaacaggtaa gtccggcctc cgcgccgggt tttggcgcct cccgcgggcg cccccctcct 4920
cacggcgagc gctgccacgt cagacgaagg gcgcagcgag cgtcctgatc cttccgcccg 4980
gacgctcagg acagcggccc gctgctcata agactcggcc ttagaacccc agtatcagca 5040
gaaggacatt ttaggacggg acttgggtga ctctagggca ctggttttct ttccagagag 5100
cggaacaggc gaggaaaagt agtcccttct cggcgattct gcggagggat ctccgtgggg 5160
cggtgaacgc cgatgatgcc tctacta                                  5187
```

| SEQ ID NO: 2 | moltype = DNA   length = 2212 |
|---|---|
| FEATURE | Location/Qualifiers |
| source | 1..2212 |
| | mol_type = other DNA |
| | organism = synthetic construct |

SEQUENCE: 2

```
gccaccatgg cggcggatgg ctatctgccg gattggctgg aagataacct gagcgaaggc 60
attcgcgaat ggtgggatct gaaaccgggc gcgccgaaac cgaaagcgaa ccagcagaaa 120
caggatgatg gccgcggcct ggtgctgccg ggctataaat atctgggccc gtttaacggc 180
ctggataaag cgaaccggt gaacgcgcg gatgcggcgg cgctggaaca tgataaagcg 240
tatgatcagc tgaaagcggg cgataaaccg tatctgcgct ataaccatgg ggatgcggaa 300
tttcaggaac gcctgcagga agataccagc tttggccgca acctgggccg cgcggtgttt 360
caggcgaaaa aacgcgtgct ggaaccgctg gcctggtgg aagaaggcgc gaaaaccgcg 420
ccgggcaaaa aacgcccggt ggaacagagc ccgcaggaac cggatagcag cagcggcatt 480
ggcaaaaccg gccagcagcc ggcgaaaaaa cgcctgaact tggccagac ggcgatagc 540
gaaagcgtgc cggatccgca gccgctgggc gaaccgcccg ggcggtgggc 600
ccgaccacca tggcgagcgg cggcggcgcg ccgatgcgg ataacaacga aggcgcggat 660
ggcgtgggca cgcgagcgg caactggcat tgcgatagca cctggctggg cgatcgcgtg 720
attaccacca gcacccgcac ctgggcgctg ccgacctata caaccatct gtataaacag 780
attagcagcg cgagcaccgg cgcgagcaac gataaccatt attttggcta tagcaccccg 840
tgggctatt ttgattttaa ccgctttcat tgccattgta gccccgcgca ttggcagccgc 900
ctgattaaca acaactgggg ctttcgcccc aaacgcctga actttaaact gtttaacatt 960
caggtgaaag aagtgaccac caacgatggc gtgaccacca ttgcgaacaa cctgaccagc 1020
accgtgcagg tgtttagcga tagcgaatat cagctgccgt atgtgctggg cagcgcgcat 1080
cagggctgcc tgcgccgtt tccggcgat tgtgttatga ttccgtatgg ctatctgacc 1140
ctgaacaacg gcagccagca ggtgggccgc agcacgtttt attgcctgga atattttccg 1200
agccagatgc tgcgcaccgg caacaacttt accttagct ataccttga agatgtgccc 1260
tttcatagca gctatgcgca tagccagagc ctggatcgcc tgatgaaccc gctgattgat 1320
cagtatctgt attttctgaa ccgcacccag aaccagagcg gcagcgcgca gaacaaagat 1380
ctgctgttta gccgcggcag cccggcgggc atgagcgtgc agccgaaaaa ctggctgccg 1440
ggcccgtgct atcgccagcg cgtgagcaaa accaaaaccg taacaacaa cagcaacttt 1500
```

```
acctggaccg gcgcgagcaa atataacctg aacggccgcg aaagcattat taacccgggc   1560
accgcgatgg cgagccataa agatgataaa gataaatttt ttccgatgag cggcgtgatg   1620
attttttggca aagaaagcgc gggcgcgagc aacaccgcgc tggataacgt gatgattacc   1680
gatgaagaag aaattaaagc gaccaacccg gtggcgaccg aacgctttgg caccgtggcg   1740
gtgaacctgc agagcagcag caccgatccg gcgaccggcg atgtgcatgt gatgggcgcg   1800
ctgccgggca tggtgtggca ggatcgcgat gtgtatctgc agggcccgat ttgggcgaaa   1860
attccgcata ccgatggcca ttttcatccg agcccgctga tgggcggctt tggcctgaaa   1920
catccgccgc cgcagattct gattaaaaac accccggtgc cggcgaaccc gccggcggaa   1980
tttagcgcga ccaaatttgc gagctttatt acccagtaga gcaccggcca ggtgagcgtg   2040
gaaattgaat gggaactgca gaaagaaaaac agcaaacgct ggaacccgga agtgcagtat   2100
accagcaact atgcgaaaag cgcgaacgtg gattttaccg tggataacaa cggcctgtat   2160
accgaaccgc gcccgattgg cacccgcttt ctgacccgcc cgctgttcta ga           2212

SEQ ID NO: 3           moltype = DNA   length = 7399
FEATURE                Location/Qualifiers
source                 1..7399
                       mol_type = other DNA
                       organism = synthetic construct
SEQUENCE: 3
accatgttca tgttttcttt ttttttctac aggtcctggg tgacgaacag ggtaccaaga     60
tctaacttgt ttattgcagc ttataatggt tacaaataaa gcaatagcat cacaaatttc    120
acaaataaag catttttttc actgcattct agttgtggtt tgtccaaact catcaatgta    180
tcttatcatg tctggatctc gacctcgact agagcatgcc tacgtagata agtagcatgg    240
cgggttaatc attaactaca aggaaccccct agtgatggag ttggccactc cctctctgcg    300
cgctcgctcg ctcactgagg ccgggcgacc aaaggtcgcc cgacgcccgg gctttgcccg    360
ggcggcctca gtgagcgagc gagcgcgcag ctggcgtaag cgcaagagg cccgcaccga    420
tcgcccttcc caacagttgc gcagcctgaa tggcgaatgg cgattccgtt gcaatggctg    480
gcggtaatat tgttctggat attaccagca aggccgatag tttgagttct tctactcagg    540
caagtgatgt tattactaat caaagaagta ttgcgacaac ggttaatttg cgtgatggac    600
agactctttt actcggtggc ctcactgatt ataaaaacac ttctcaggat tctggcgtac    660
cgttcctgtc taaaatcccct ttaatcggcc tcctgtttag ctcccgctct gattctaacg    720
aggaaagcac gttatacgtg ctcgtcaaag caaccatagt acgcgccctg tagcggcgca    780
ttaagcgcgg cgggtgtggt ggttacgcgc agcgtgaccg ctacacttgc cagcgcccta    840
gcgcccgctc ctttcgcttt cttccccttcc tttctcgcca cgttcgccgg ctttccccgt    900
caagctctaa atcggggggct ccctttaggg ttccgattta gtgctttacg gcacctcgac    960
cccaaaaaac ttgattaggg tgatggttca cgtagtgggc catcgccctg atagacggtt   1020
tttcgccctt tgacgttgga gtccacgttc tttaatagtg gactcttgtt ccaaactgga   1080
acaacactca accctatctc ggtctattct tttgatttat aagggatttt gccgatttcg   1140
gcctattggt taaaaaatga gctgatttaa caaaaattta acgcgaattt taacaaaata   1200
ttaacgttta caatttaaat atttgcttat acaatcttcc tgtttttggg gcttttctga   1260
ttatcaaccg gggtacatat gattgacatg ctagttttac gattaccgtt catcgattct   1320
cttgtttgct ccagactctc aggcaatgac ctgatagcct ttgtagagac ctctcaaaaa   1380
tagctaccct ctccggcatg aatttatcag ctagaacggt tgaatatcat attgatggtg   1440
atttgactgt ctccgccctt ctctcacccgt ttgaatcttt acctacacat tactcaggca   1500
ttgcatttaa aatatatgag ggttctaaaa attttttatcc ttgcgttgaa ataaaggctt   1560
ctcccgcaaa agtattacag ggtcataatg ttttttggtac aaccgattta gctttatgct   1620
ctgaggcttt attgcttaat tttgctaatt cttttgcttg cctgtatgat ttattggatg   1680
ttggaattcc tgatgcggta ttttctcctt acgcatctgt gcggtatttc acaccgcata   1740
tggtgcactc tcagtacaat ctgctctgat gccgcatagt taagcagcc ccgacacccg   1800
ccaacacccg ctgacgcgcc ctgacgggct tgtctgctcc cggcatccgc ttacagacaa   1860
gctgtgaccg tctccgggag tgcatgtgt cagaggtttt caccgtcatc accgaaacgc   1920
gcgagacgaa agggcctcgt gatacgccta ttttttatagg ttaatgtcat gataataatg   1980
gtttcttaga cgtcaggtgg cacttttcgg ggaaatgtgc gcggaacccc tatttgttta   2040
tttttctaaa tacattcaaa tatgtatccg ctcatgagac aataaccctg ataaatgctt   2100
caataatatt gaaaaaggaa gagtatgagt attcaacatt tccgtgtcgc ccttattccc   2160
ttttttgcgg cattttgcct tcctgttttt gctcacccag aaacgctggt gaaagtaaaa   2220
gatgctgaag atcagttggg tgcacgagtg ggttacatcg aactggatct caacagcggt   2280
aagatccttg agagttttcg ccccgaagaa cgttttccaa tgatgagcac ttttaaagtt   2340
ctgctatgtg gcgcggtatt atcccgtatt gacgccgggc aagagcaact cggtcgccgc   2400
atacactatt ctcagaatga cttggttgag tactcaccag tcacagaaaa gcatcttacg   2460
gatggcatga cagtaagaga attatgcagt gctgccataa ccatgagtga taacactgcg   2520
gccaacttac ttctgacaac gatcggagga ccgaaggagc taaccgcttt tttgcacaac   2580
atgggggatc atgtaactcg ccttgatcgt tgggaaccgg agctgaatga agccatacca   2640
aacgacgagc gtgacaccac gatgcctgta gcaatggcaa caacgttgcg caaactatta   2700
actggcgaac tacttactct agcttcccgg caacaattaa tagactggat ggaggcggat   2760
aaagttgcag gaccacttct gcgctcggcc cttccggctg gctggtttat tgctgataaa   2820
tctggagccg gtgagcgtgg gtctcgcggt atcattgcag cactgggcc agatggtaag   2880
ccctccgta tcgtagttat ctacacgacg gggagtcagg caactatgga tgaacgaaat   2940
agacagatcg ctgagatagg tgcctcactg attaagcatt ggtaactgtc agaccaagtt   3000
tactcatata ctttagat tgatttaaaa cttcatttt aatttaaaag gatctaggtg   3060
aagatccttt ttgataatct catgaccaaa atcccttaac gtgagttttc gttccactga   3120
gcgtcagacc ccgtagaaaa gatcaaagga tcttcttgag atcctttttt tctgcgcgta   3180
atctgctgct tgcaaacaaa aaaaccaccg ctaccagcgg tggtttgttt gccggatcaa   3240
gagctaccaa ctctttttcc gaaggtaact ggcttcagca gagcgcagat accaaatact   3300
gtccttctag tgtagccgta gttaggccac cacttcaaga actctgtagc accgcctaca   3360
tacctcgctc tgctaatcct gttaccagtg gctgctgcca gtggcgataa gtcgtgtctt   3420
accgggttgg actcaagacg atagttaccg gataaggcgc agcggtcggg ctgaacgggg   3480
ggttcgtgca cacagcccag cttggagcga acgacctaca ccgaactgag atacctacag   3540
cgtgagctat gagaaagcgc cacgcttccc gaagggagaa aggcggacag gtatccggta   3600
```

-continued

```
agcggcaggg tcggaacagg agagcgcacg agggagcttc caggggaaa cgcctggtat  3660
ctttatagtc ctgtcgggtt tcgccacctc tgacttgagc gtcgattttt gtgatgctcg  3720
tcagggggc ggagcctatg gaaaaacgcc agcaacgcgg ccttttacg gttcctggcc  3780
ttttgctggc cttttgctca catgttcttt cctgcgttat ccctgattc tgtggataac  3840
cgtattaccg cctttgagtg agctgatacc gctcgccgca gccgaacgac cgagcgcagc  3900
gagtcagtga gcgaggaagc ggaagagcgc ccaatacgca aaccgcctct ccccgcgcgt  3960
tggccgattc attaatgcag ctgcgcgctc gtcgctcac tgaggccgcc cgggcaaagc  4020
ccgggcgtcg ggcgaccttt ggtcgcccgg cctcagtgag cgagcgagcg cgcagagagg  4080
gagtggccaa ctccatcact aggggttcct tgtagttaat gattaacccg ccatgctact  4140
tatctacgta gccatgctct aggacattga ttattgacta gtggagttcc gcgttacata  4200
acttacggta aatggcccgc ctggctgacc gcccaacgac ccccgcccat tgacgtcaat  4260
aatgacgtat gttcccatag taacgccaat agggactttc cattgacgtc aatgggtgga  4320
gtatttacgg taaactgccc acttggcagt acatcaagtg tatcatatgc caagtacgcc  4380
ccctattgac gtcaatgacg gtaaatggcc cgcctggcat tatgcccagt acatgaccct  4440
atgggacttt cctacttggc agtacatcta cgtattagtc atcgctatta ccatggtcga  4500
ggtgagcccc acgttctgct tcactctccc catctcccc ccctcccac cccaattt  4560
gtatttattt atttttttaat tattttgtgc agcgatgggg gcggggggg ggggggcgc  4620
gcgccaggcg gggcggggcg gggcgagggg cggggccgca aggtgcggcg  4680
gcagccaatc agagcggcgc gctccgaaag tttccttta tggcgaggcg gcggcggcgg  4740
cggccctata aaaagcgaag cgcgcggcgg gcgggagtcg ctgcgcgctg ccttcgcccc  4800
gtgccccgct ccgccgccgc ctcgcgccgc ccgcccgg tctgactgac cgcgttacta  4860
aaacaggtaa gtccggcctc cgcgccgggt tttggcgcct cccgcgggcg ccccctcct  4920
cacggcgagc gctgccacgt cagacgaagg gcgcagcgag cgtcctgatc cttccgcccg  4980
gacgctcagg acagcggccc gctgctcata agactcggcc ttagaacccc agtatcagca  5040
gaaggacatt ttaggacggg acttgggtga ctctagggca ctggttttct ttccagagag  5100
cggaacaggc gaggaaaagt agtcccttct cggcgattct gcggagggat ctccgtgggg  5160
cggtgaacgc cgatgatgcc tctactagcc accatggcgg cggatggcta tctgccggat  5220
tggctggaag ataacctgag cgaaggcatt cgcgaatggt gggatctgaa accgggcgcg  5280
ccgaaaccga aagcgaacca gcagaaacag gatgatggcc gcggcctggt gctgccgggc  5340
tataaatatc tgggcccgtt taacggcctg gataaaggcg aaccggtgaa cgcggcggat  5400
gcggcggcgc tggaacatga taaagcgtat gatcagctga aagcgggcga taaccctgat  5460
ctgcgctata accatgcgga tgcggaattt caggaacgcc tgcaggaaga taccagcttt  5520
ggcggcaacc tgggccgcgc ggtgtttcag gcgaaaaaac gcgtgctgga accgctgggc  5580
ctggtggaag aaggcgcgaa aaccgcgccg ggcaaaaaac gcccggtgga acagagcccg  5640
caggaaccgg atagcagcag cggcattggc aaaaccggcc agcagccggc gaaaaaacgc  5700
ctgaactttg gccagaccgg cgatagcgaa agcgtgccgg atccgcagcc gctgggcgaa  5760
ccgccggcga ccccggcggc ggtgggcccg accaccatgg cgagcggcgg cggcgcgccg  5820
atggcggata caacgaagg cgcggatggc gtgggcaacg cgagcggcaa ctggcattgc  5880
gatagcacct ggctgggcga tcgcgtgatt accaccagca cccgcacctg ggcgctgccg  5940
acctataaca accatctgta taaacagatt agcagcgcga gcaccggcgc gagcaacgat  6000
aaccattatt ttggctatag caccccgtgg ggctattttg attttaaccg ctttcattgc  6060
cattttagcc cgcgcgattg gcagcgcctg attaacaaca actggggctt tcgcccgaaa  6120
cgcctgaact ttaaactgtt taacattcag gtgaaagaag tgaccaccaa cgatggcgtg  6180
accaccattg cgaacaacct gaccagcacc gtgcaggtgt ttagcgatag cgaatatcag  6240
ctgccgtatg tgctgggcag cgcgcatcag ggctgcctgc cgccgtttcc ggcggatgtg  6300
tttatgattc cgtatggcta tctgaccctg aacaacggca gccaggcggt gggccgcagc  6360
agcttttatt gcctggaata ttttccgagc cagatgctgc gcaccggcaa caactttacc  6420
tttagctata cctttgaaga tgtgccgttt catagcagct atgcgcatag ccagagcctg  6480
gatcgcctga tgaacccgct gattgatcag tatctgtatt ttctgaaccg cacccagaac  6540
cagagcggca gcgcgcagaa caaagatctg ctgtttagcc gcggcagccc ggcgggcatg  6600
agcgtgccag cgaaaaactg gctgccgggc ccgtgctatc gccagcgcgt gagcaaaacc  6660
aaaaccgata acaacaacag caactttacc tggaccggcg cgagcaaata taacctgaac  6720
ggccgcgaaa gcattattaa cccgggcacc gcgatggcga gccataaaga tgataaagat  6780
aaatttttc cgatgagcgg cgtgatgatt tttggcaaag aaagcgcggg cgcgagcaac  6840
accgcgctgg ataacgtgat gattaccgat gaagaagaaa ttaaagcgac caacccggtg  6900
gcgaccgaac gctttggcac cgtggcggtg aacctgcaga gcagcagcac cgatccggcg  6960
accggcgatg tgcatgtgat gggcgcgctg ccgggcatgg tgtggcagga tcgcgatgtg  7020
tatctgcagg gcccgatttg ggcgaaaatt ccgcataccg atggccattt tcatccgagc  7080
ccgctgatgg gcggctttgg cctgaaacat ccgccgccgc agattctgat taaaaacacc  7140
ccggtgccgg cgaacccgcc ggcggaattt agcgcgacca aatttgcgag ctttattacc  7200
cagtatagca ccggccaggt gagcgtggaa attgaatggg aactgcagaa agaaaacagc  7260
aaaacgctgg acccggaagt gcagtatacc agcaactatg cgaaaagcgc gaacgtggat  7320
tttaccgtgg ataacaacgg cctgtatacc gaaccgcgcc cgattggcac ccgctttctg  7380
acccgcccgc tgttctaga                                              7399
```